(12) United States Patent
von Borstel et al.

(10) Patent No.: US 6,919,320 B1
(45) Date of Patent: Jul. 19, 2005

(54) PHARMACEUTICAL COMPOSITIONS CONTAINING DEOXYRIBONUCLEOSIDES FOR WOUND HEALING

(75) Inventors: Reid Warren von Borstel, Kensington, MD (US); Michael Kevin Bamat, Chevy Chase, MD (US)

(73) Assignee: Wellstat Therapeutics Corporation, Gaithersburg, MD (US)

(*) Notice: Subject to any disclaimer, the term of this patent is extended or adjusted under 35 U.S.C. 154(b) by 0 days.

(21) Appl. No.: 08/473,331

(22) Filed: Jun. 7, 1995

Related U.S. Application Data

(60) Division of application No. 08/419,767, filed on Apr. 10, 1995, now Pat. No. 5,770,582, which is a continuation of application No. 08/096,407, filed on Jul. 26, 1993, now abandoned, which is a division of application No. 07/911,379, filed on Jul. 13, 1992, now Pat. No. 5,246,708, which is a continuation of application No. 07/341,925, filed on Apr. 21, 1989, now abandoned, which is a continuation-in-part of application No. 07/186,031, filed on Apr. 25, 1988, now abandoned, which is a continuation-in-part of application No. 07/115,923, filed on Oct. 28, 1987, now abandoned.

(51) Int. Cl.[7] .......................... A61K 31/70; A01N 25/00
(52) U.S. Cl. ............................ 514/45; 514/46; 514/47; 514/48; 514/49; 514/50; 514/51; 514/944; 514/969; 536/27.1; 536/27.14; 536/27.21; 536/28.1; 536/28.5
(58) Field of Search .............................. 514/45–51, 944; 514/969; 536/27.1, 27.14, 27.21, 28.1, 28.5

(56) References Cited

U.S. PATENT DOCUMENTS

| | | | |
|---|---|---|---|
| 3,856,776 A | 12/1974 | Cehovic | |
| 3,860,706 A | 1/1975 | Ikeda | |
| 3,894,000 A | 7/1975 | Wechter | |
| 3,991,045 A | 11/1976 | Ishida | |
| 4,208,406 A | 6/1980 | Lapinet | |
| 4,560,678 A | 12/1985 | Ranson | |
| 4,657,896 A | 4/1987 | Yano | |
| 4,757,139 A | 7/1988 | Kawaguchi | |
| 4,758,553 A | 7/1988 | Ogoshi | |
| 5,770,582 A | * 6/1998 | von Borstel et al. | 514/45 |

FOREIGN PATENT DOCUMENTS

| | | |
|---|---|---|
| CA | 835941 | 11/1964 |
| EP | 0222192 | 5/1987 |
| FR | AL 2556727 | 6/1985 |
| GB | 2152814 A | 8/1985 |

OTHER PUBLICATIONS

Savkovic et al, Int. J. Rad. Biol. 9:361–368 (1965).
Smets et al, Int. J. Rad. Biol. 13:269–273 (1967).
Soska et al, Folia Biologica 5:190–198 (1959).
Sugahara et al, Brookhaven Symposia in Biology, 284–302 (1967).
Wagner, Int. J. Rad. Biol. 12:101–112 (1967).
Wilczok et al, Int. J. Rad. Biol. 9:201–211 (1965).
Goyanes–Villaescusa et al, Lancet 2:575–576 (1973).
Dumont, Ann. Surg. 150:799–807 (1959).
Nicolau et al, Der Hautarzt, 17:512–515 (1966).
Marshak et al, Proc. Soc. Exp. Biol. Med. 58:62–63 (1945).
Newman et al, Am. J. Physiol. 164:251–253 (1951).
Casida et al, Biochemical Pharmacology 15:627–644 (1966).
Rosowsky et al, Cancer Treatment Reports 65:93–99 (Jan./Feb. 1981).
Ensminger et al, Biochemical Pharmacology 28:1541–1545 (Oct. 1978).
Fridovich, Annu. Rev. Biochem. 44:147–159 (1975).
Szoka, Jr. et al, Proc. Natl. Acad. Sci., vol. 75, No. 9, p. 4194–4198 (1978).
Wechter et al, Journal of Med. Chem. 18, No. 4, p. 339–344 (1975) "Ara–Cytidine Acylates. Use of . . . Relationship Correlation [1,2]".
Wechter et al, Journal of Medicinal Chemistry, 19, No. 8, p. 1013–1016 (1976) "Nucleic Acids. 16. Orally . . . Cytidine[1,2]".
Szoka et al, Biochemistry, 75, No. 9, p. 4194–4198 (Sep. 1978) "Procedure for Preparation of Liposomes . . . Evaporation".
DeLapp et al, J. Investigative Dermatology 66:306–312 (1976) "Importance of Pyrimidine . . . In Skin".
Snyder, R.D., Mutation Research, 131 p. 163–172 (1984) "The Role of Deoxynucleoside . . . By Hydroxyurea".
Okabe et al, Digestive Diseases, vol. 16, No. 3, p. 277–283 (Mar. 1971) "A Method for Experimental, . . . Ulcers in Rats".
1988 Physician's Desk Reference, pp. 1551–1552.
Braun et al, Proc. Soc. Exptl. Biol. Med. 119:701–707 (1965).
Martin et al, 1987, J. of Pharmaceutical Sciences, vol. 76, No. 2, p 180–184.
Kanazir et al, Bull. Inst. Nuc. Sci. "Boris, Kidrich" 9:145–153 (1959).
Beltz et al, Bioch. Biophys. Acta 297:258–267 (1973).
Hunting D.J., et al, Carcinogenesis 6:1525–1528 (1985).
Golba, et al, Int. J. Rad. Biol. 13:261–268 (1967).
Goh, et al, Proc. Soc. Exp. Biol. Med. 145:938–943 (1974).
Horikawa et al, Exp. Cell Res. 34:198–200 (1964).
Pantic et al, Nature 193:993–994 (1962).
Paoletti et al, Rev. Francais, Etudes Clin. et Bio. 9:950–955 (1964).
Petrovic et al, Int. J. Radiat. Biol. 18:243–258 (1970).
Petrovic et al, Studia Biophysica 43:13–18 (1974).
Petrovic et al, Int. J. Radiat. Res. 11:609–611 (1967).
Savkovic et al, Nature 203:1297–1298 (1964).
Savkovic et al, Nature 211:1179–1180 (1966).

* cited by examiner

*Primary Examiner*—James O. Wilson
*Assistant Examiner*—Howard V. Owens
(74) *Attorney, Agent, or Firm*—Nixon & Vanderhye

(57) ABSTRACT

The invention relates to compositions comprising 2'-deoxyribonucleosides. The invention also relates to methods of accelerating the healing of wounds, abrasions, cuts, incisions, and superficial burns induced by heat, sunlight, chemical agents, or infections, and methods for ameliorating the effects of aging of the epidermal tissues comprising administering the compositions of the present invention to an animal.

7 Claims, 9 Drawing Sheets

PHARMACEUTICAL COMPOSITIONS CONTAINING DEOXYRIBONUCLEOSIDES FOR WOUND HEALING

This is a Divisional of application Ser. No. 08/419,767, filed Apr. 10, 1995 now U.S. Pat. No. 5,770,582, which is a Continuation of Ser. No. 08/096,407 filed Jul. 26, 1993, abandoned, which is a Divisional of Ser. No. 07/911,379, filed Jul. 13, 1992, now U.S. Pat. No. 5,246,708; which is a Continuation of Ser. No. 07/341,925, filed Apr. 21, 1989 now abd; which is a CIP of Ser. No. 07/186,031 filed Apr. 25, 1988, abandoned; which is a CIP of Ser. No. 07/115,923, filed Oct. 28, 1987 now abandoned.

FIELD OF THE INVENTION

This invention relates generally to the use of novel combinations of 2'-deoxyribonucleosides and 2'-deoxyribonucleotides and to the use of these compounds in pharmaceutical carriers to promote wound healing. More specifically, this invention relates to novel combinations of two or more of 2'-deoxyadenosine, 2'-deoxyguanosine, 2'-deoxycytidine and 2'-deoxythymidine and/or their corresponding nucleotides and their applications, locally or topically in a mixture with carrier compounds to increase the supply of the active components to animal tissue and thereby to support cellular metabolic functions. Even more specifically, this invention relates to the use of mixtures of these compounds in carriers to promote and accelerate the healing of wounds, surgical incisions, lesions or ulcers of the gastrointestinal tract, burns induced by heat, ultraviolet light, or chemical agents, and superficial tissue damage caused by infections.

BACKGROUND OF THE INVENTION

The healing of wounds or related forms of tissue damage generally depends on cellular proliferation and the formation of new connective, endothelial, and epithelial tissue. An agent which stimulates or accelerates the cellular processes involved in wound healing would have great value in medical practice and could be used to improve or speed the healing of many types of wounds or lesions, including surgical incisions, burns induced by heat, chemicals, or irradiation, abrasions, lacerations, amputations, ischemic or decubitus ulcers, lesions or ulcers of the mouth, stomach or intestines, skin graft donor sites, and corneal lesions. Such agents may also be important in improving the acceptance of skin or corneal transplants, and in promoting the repair or damaged cartilage or bone.

Agents which accelerate or improve wound healing would be particularly valuable under physiological conditions in which wound healing is impaired, such as in diabetic patients, or in subjects undergoing cancer chemotherapy (e.g. with adriamycin or cyclophosphamide) or corticosteroid treatment, or in patients after therapeutic or accidental exposure to ionizing radiation.

Several agents have been reported to favorably influence the cellular processes involved in wound healing, e.g., polypeptid growth factors, allantoin, Vitamin A (and derivatives), zinc, exogenous DNA, and aloe vera preparations. These compounds operate through various poorly defined mechanisms and display varying degrees of effectiveness in particular applications.

Deoxyribonucleic acid (DNA) has been used to accelerate wound cicatrization or healing. Dumont, Ann. Surg. 150:799 (1959) discloses that exogenous DNA applied to experimental wounds in rabbit ears, accelerated the growth of granulation tissue in the wounds. A mixture of DNA plus deoxyribonuclease (the enzyme primarily responsible for degradation of DNA) was more effective in accelerating fibroplasia than either DNA or deoxyribonuclease alone. The total amount of granulation tissue formed after treatment with DNA was not greater than in untreated controls; the onset and rate of its growth were, however, significantly accelerated. The authors suggest that low polymer DNA fragments are the actual active agents.

Nicolau and Badanoiu, Der Hautartzt, 17:512 (1966) treated experimental skin wounds on the backs of rats daily with intralesion injection of a 1% solution of DNA in physiological saline. The wounds treated with local injection of DNA were cicatrized within four to eight days, while those treated with only saline were cicatrized after ten to fifteen days. A 2% solution of DNA similarly injected into the wounds caused tissue necrosis.

Marshak and Walker, Proc. Soc. Exp. Biol. Med. 58:62 (1945) applied DNA to experimental skin wounds in rats and found significant acceleration of the growth of granulation tissue within the wounds, as compared to untreated controls. Although the granulation tissue appeared sooner in treated wounds, the final amount of granulation tissue was no greater than in untreated wounds.

Ranson (U.S. Pat. No. 4,560,678) discloses a topical formulation containing DNA and allantoin that was used to treat leg ulcers of venous origin. Flecchia (French Patent 2,556,727) discloses a composition containing DNA and bacteriocidal quaternary ammonium compounds for treatment of wounds. U.S. Pat. No. 4,657,896 discloses the use of DNA for treatment of digestive ulcer symptoms particularly when administered parenterally. While local administration of DNA may be effective in promoting wound healing, there are several significant disadvantages to utilization of DNA per se in pharmaceutical preparations which may limit its clinical utility or acceptance. DNA, being extracted from animal tissues, contains other biological materials, e.g., histones or other proteins, which may be antigenic. It is difficult to remove these other biological materials, and, accordingly, commercial high purity DNA is typically about 0.5% protein. In addition, DNA from natural sources may not be uniform from batch to batch. DNA may also have undesirable biological activity beyond its role as a wound healing agent. For example, double-stranded nucleic acids induce interferon formation, probably through interaction with undefined sites on the surface of fibroblasts or lymphocytes. Such effects may not be beneficial and may even be detrimental to wound healing or other biological processes.

DNA also contains phosphate (equimolar to the content of nucleosides) and topical application to wounds may result in high local concentrations of phosphate as the DNA is metabolized. This may be detrimental to the wound healing process and may account for the tissue necrosis that was observed after administration of 2% DNA in the studies of Nicolau et al. Lastly, exogenous DNA can be incorporated into cellular DNA and thereby introduce exogenous functional genes into cells. This is clearly undesirable, particularly if the introduced DNA sequence is that of a virus or oncogene.

U.K. Patent Application No. 2,152,814A to Ogoshi relates to compositions for nutritional replenishment which contain at least two nucleic acid compounds selected from: (a) nucleic acid bases, (b) nucleosides, and (c) nucleotides or salts thereof. The compositions which may be administered parenterally or enterally are said to be capable of enhancing the efficient use of amino acids in the body and of assuring satisfactory nutrition control and maintenance of nitrogen balance.

Japanese Patent No. 60028929 discloses the use of orally administered deoxyguanosine for preventing the formation of stress-induced gastric ulcers in rats. No data were provided concerning the effect (if any) of deoxyguanosine on the healing of gastric ulcers.

U.S. Pat. No. 4,208,406, Lapinet, discloses the use of cyclic 3',5'-adenosine monophosphate (cyclic AMP) as a topical antiinflammatory and healing agent.

While the strategy of delivering healing agents which include inter alia DNA to wounds to accelerate wound healing has been recognized, there remains a need for more effective compositions for the healing of wounds, burns, and other lesions which do not cause undesirable side effects.

OBJECTS OF THE INVENTION

It is a primary object of this invention to provide novel compounds and pharmaceutical products which can efficiently promote accelerated healing of wounds, ulcers, burns, and other types of lesions.

It is a further object of this invention to provide a family of effective wound healing agents which are nonantigenic and do not carry genetic information.

It is still a further object of this invention to provide a family of effective wound healing agents which are inexpensive, uniform and stable.

It is still a further object of this invention to provide wound healing agents which can be effectively administered locally, which have no undesirable toxic effects, and which can be administered to animals and humans to effectively promote healing of wounds, ulcers, burns, and other types of lesions.

It is a further and related object of this invention to provide effective wound healing agents which can be applied locally or topically in a variety of delivery vehicles.

SUMMARY OF THE INVENTION

These and other objects of the invention are achieved by the administration of novel mixtures of 2'-deoxyribonucleosides, preferably incorporated in carrier compositions, to improve the healing of wounds, or repair damaged tissues, and in the treatment of other physiological and pathological tissue conditions which may be appropriately treated by application or instillation of a topical or local preparation to accelerate healing.

Broadly, the invention is in mixtures of 2'-deoxyribonucleosides in particular ratios dissolved or suspended in suitable pharmaceutical carriers. While the application of single 2'-deoxyribonucleosides alone to experimental wounds has been found to produce little or no acceleration of wound healing, specific mixtures of two or more different 2'-deoxyribonucleosides have been found to accelerate the healing of experimental wounds. Each specific mixture produces a characteristic healing response.

More particularly, it has been found that the combination of 2'-deoxyribonucleosides, 2'-deoxycytidine and 2'-deoxyguanosine, produces a substantial increase in the rate of healing of experimental wounds compared to controls and other two-way combinations. The compositions may contain (a) a major amount of 2'-deoxycytidine and an effective amount of 2'-deoxyguanosine, or, (b) a major amount of 2'-deoxyguanosine and an effective amount of 2'-deoxycytidine. Desirably the binary composition contains from 10% to 90% (by mole) 2'-deoxycytidine and 90% to 10% 2'-deoxyguanosine. Preferred compositions contain from 25% to 75% of the two components.

Three component combinations of 2'-deoxycytidine, 2'-deoxyguanosine, and 2'-deoxyadenosine, as well as three-component combinations of 2'-deoxycytidine, 2'-deoxyguanosine, and 2'-deoxythymidine also produce substantial increases in the rate of healing of experimental wounds compared to controls and other three-way combinations. Four component combinations of 2'-deoxycytidine, 2'-deoxyguanosine, 2'-deoxyadenosine, and 2'-deoxythymidine are the most effective in improving the rate of healing of experimental wounds.

The three and four component compositions contain effective amounts of 2'-deoxycytidine and 2'-deoxyguanosine, typically 50% or more of the binary mixtures as described above.

The wound healing compositions contain the 2'-deoxyribonucleosides and/or their corresponding 3' and/or 5' phosphate ester derivatives. These compounds may be further substituted and may be in free or pharmaceutically acceptable salt form.

The mixtures of 2'-deoxyribonucleosides, preferably in pharmaceutical carriers, accelerate the rate of wound healing by delivering 2'-deoxyribonucleosides to areas of damaged tissue. The preparation of the invention may be administered in combination with any of a variety of conventional pharmaceutical carriers, ointments, gels, pastes, suppositories, sprays or irrigation solutions, or may be incorporated into carriers including liposomes, polymers or biodegradable polymers for gradual release, or from impregnated bandages, sutures, and similar materials.

The compositions of the invention may be used to promote healing of any type of wound, including cuts, incisions, abrasions, burns, and the like, which may be treated by the administration of a local, especially topical, preparation, or by the application of any other material which may hold and release a supply of the appropriate mixture of 2'-deoxyribonucleosides.

BRIEF DESCRIPTION OF THE DRAWINGS

The invention as well as other objects, features and advantages thereof will be understood more clearly and fully from the following detailed description, when read with reference to the accompanying drawings, in which.

DETAILED DESCRIPTION OF THE INVENTION

Figure 1:
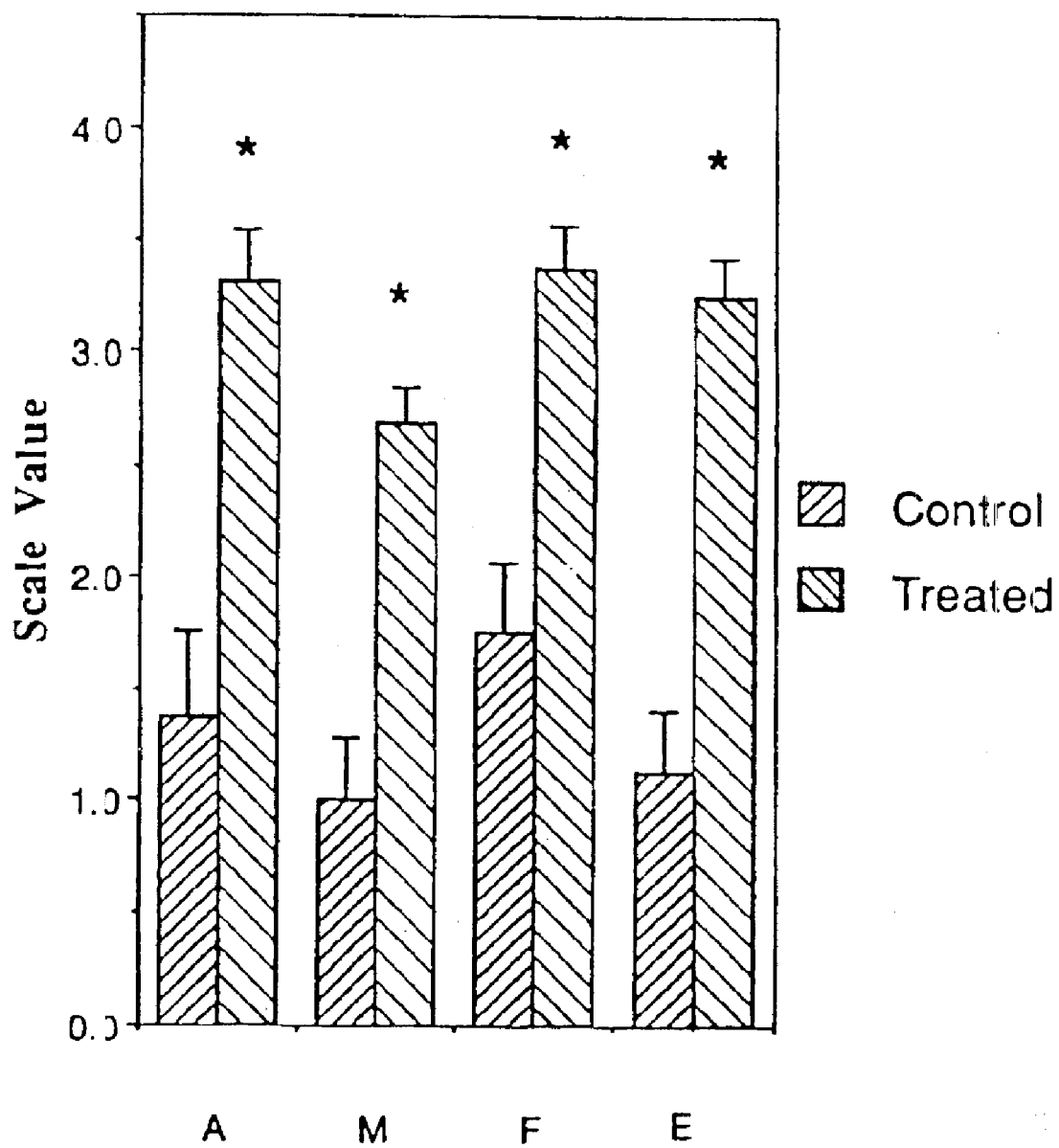
FIG. 1 shows the scale values for four wound-healing parameters, degree of angiogenesis (A), macrophage density (M), fibroblast density (F), and epithelial coverage (E), in control rats and rats treated with the combination of 2'-deoxyadenosine, 2'-deoxycytidine, 2'-deoxyguanosine, and 2'-deoxythymidine for one week. All rats were pretreated with dexamethasone in order to retard wound healing. Scale values are: 0=absent, 1=minimal, 2=mild, 3=moderate, and 4=marked. The * indicates statistically significant differences compared to control values in this and all subsequent figures.

In its broadest aspects, the invention is in a discovery that a composition of matter comprising from 10 to 90 percent by mol of 2'-deoxycytidine and from 90 to 10 percent by mol 2'-deoxyguanosine, or the pharmaceutically acceptable salts thereof, has very significant activity in wound healing applications. It has been discovered that the binary mixtures of 2'-deoxycytidine and 2'-deoxyguanosine, preferably those mixtures wherein each of the two components is present in from 25 to 75 percent of the composition, when applied locally or topically to wounds, including cuts, incisions, abrasions, burns, and the like, substantially increase the rate of healing. While other wound healing materials may be included in the compositions of the invention, the active wound healing agents consist essentially of the binary mixtures of 2'-deoxycytidine and 2'-deoxyguanosine.

The 2'-deoxyribonucleosides may be present in their free form or as the corresponding nucleotides, i.e., a 3', a 5' or a 3',5' phosphate ester derivative. Alternatively, the 2'-deoxyribonucleosides may be present as substituted derivatives of either the free form or the nucleotide form. The substituted derivatives of 2'-deoxycytidine and 2'-deoxyguanosines include compounds substituted at one or both hydroxyl groups in the deoxyribose moiety and/or substituted in the exocyclic amine on the purine ring of 2'-deoxyguanosine or in the exocyclic amine on the pyrimidine ring of 2'-deoxycytidine by a radical selected from the group consisting of biocompatible acyl radicals containing 2 to 20 carbon atoms. Where there is more than one substituent, the substituents may be the same or different. The active components may also be present as pharmaceutically acceptable salts of the 2'-deoxyribonucleosides or their derivatives. In this context, the substituted derivatives are preferably enzymatically converted back to nucleosides after application to tissues. Thus, the derivatives may serve as a vehicle for sustained delivery of nucleosides to tissues or may have other advantages in pharmaceutical formulations.

The effective binary mixtures described above may be contained in compositions of matter adapted to promote wound healing which contain a pharmaceutically acceptable carrier and, if desired, other wound healing agents. Typically, the carrier is one adapted for local or topical administration.

The binary mixtures described may be combined with 2'-deoxyadenosine, 2'-deoxythymidine, or mixtures of 2'-deoxyadenosine and 2'-deoxythymidine. Good results are obtained with wound healing compositions of matter which comprise an effective amount of the binary mixture of 2'-deoxycytidine and 2'-deoxyguanosine, as described, and additionally, either (or both) 2'-deoxyadenosine or 2'-deoxythymidine. Desirably, the binary mixture of 2'-deoxycytidine and 2'-deoxyguanosine is present in at least 50 mol percent of the overall composition and the 2'-deoxycytidine and 2'-deoxyguanosine are present in that binary mixture in from 25 to 75 percent thereof. The 2'-deoxycytidine, 2'-deoxyguanosine, 2'-deoxyadenosine, and 2'-deoxythymidine may be present as the free forms thereof, as nucleotides, or as substituted derivatives of the free form or nucleotide form.

The substituted derivatives of 2'-deoxycytidine and 2'-deoxyguanosine include compounds substituted at one or both hydroxyl groups in the deoxyribose moiety and/or substituted in the exocyclic amine on the purine ring of 2'-deoxyguanosine or in the exocyclic amine on the pyrimidine ring of 2'-deoxycytidine by a radical selected from the group consisting of biocompatible acyl radicals containing 2 to 20 carbon atoms. Where there is more than one substituent, the substituents may be the same or different.

The substituted derivatives of 2'-deoxyadenosine include compounds substituted at one or both hydroxyl groups in the deoxyribose moiety and/or substituted in the exocyclic amine on the purine ring thereof by a radical selected from the group consisting of biocompatible acyl radicals containing 2 to 20 carbon atoms. Where there is more than one substituent, the substituents may be the same or different.

The substituted derivatives of 2'-deoxythymidine include compounds substituted at one or both hydroxyl groups in the deoxyribose moiety by one or more biocompatible acyl radicals containing 2 to 20 carbon atoms which may be the same or different.

The active components may also be present as pharmaceutically acceptable salts.

Wound healing compositions of matter containing the binary mixture and 2'-deoxyadenosine or, respectively, 2'-deoxythymidine, can advantageously be prepared using pharmaceutically acceptable carriers adapted for local or topical administration.

Best results are obtained with quarternary mixtures containing an effective amount, preferably at least 50 mol percent of the overall composition, of a mixture of 10 to 90 percent by mol 2'-deoxycytidine and 90 to 10 percent by mol 2'-deoxyguanosine, and, 2'-deoxyadenosine, and 2'-deoxythymidine. The 2'-deoxyribonucleosides, as in the binary and ternary mixtures described above, may be present as their pharmaceutically acceptable salts. Desirably, the binary mixture of 2'-deoxycytidine and 2'-deoxyguanosine contains at least 25 mol percent of each of those two components. The four 2'-deoxyribonucleosides may be present in their free form, as a 3', a 5', or a 3',5' phosphate ester derivative, or as a substituted derivative, as described above, of either the free form or the nucleotide form. Advantageous compositions may be prepared using carriers adapted for local or topical administration.

The mixtures of active components may be prepared by mixing individual free form, nucleotide or derivatized components, or may be prepared by hydrolysis or DNA without separating the component nucleosides or nucleotides.

The discovery that deoxyribonucleosides are effective in promoting wound healing opens several important opportunities for administration of these agents. For ease of description, in the following discussion deoxyribonucleosides may be understood to include the free form, the nucleotide form, substituted derivatives, and mixtures thereof.

A preferred strategy is to administer these compounds locally or topically in gels, ointments, solutions, impregnated bandages, liposomes, biodegradable microcapsules or artificial skin containing the natural nucleosides. Unlike DNA, the deoxyribonucleosides contain no genetic information and are not antigenic. They are also chemically stable and can be purified easily and incorporated into a range of compositions. DNA, in contrast, is labile and easily broken into oligonucleotide fragments with random molecular weights and accordingly is unsuitable for incorporation in pharmaceutical preparations that require standards for uniformity and stability.

Compositions or dosage forms for topical application may include solutions, lotions, ointments, creams, gels, suppositories, sprays, aerosols, suspensions, dusting powder, impregnated, bandages and dressings, liposomes, biodegradable polymers, and artificial skin. Typical pharmaceutical carriers which make up the for going compositions include alginates, carboxymethylcellulose, methylcellulose, agarose, pectins, gelatins, collagen, vegetable oils, mineral oils, stearic acid, stearyl alcohol, petrolatum, polyethylene glycol, polysorbate, polylactate, polyglycolate, polyanhydrides, phospholipids, polyvinylpyrrolidone, and the like.

The concentrations of deoxyribonucleosides in pharmaceutically acceptable carriers may range from 0.1 to 20%. The dose used in a particular formulation or application will be determined by the requirements of the particular type of tissue lesion and the constraints imposed by the characteristics and capacities of the carrier materials. For a suntan lotion, 0.1 to 5% by weight of the above compositions may be added.

The compositions described above may be combined or used together or in coordination with an antibiotic, antifungal, or antiviral substance or substances to accelerate the healing of sores or other infection-damaged tissue simultaneously or in coordination with the treatment of the underlying infection. In addition, the 2'-deoxyribonucleosides of the invention may be combined with or used simultaneously or in coordination with other tissue healing promoters, such as epidermal growth factor, fibroblast growth factor, platelet derived growth factor, transforming growth factor alpha, transforming growth factor beta, and insulin-like growth factor 1 (Brunt, J. V., and Tilansner, A., Biotechnology 6:25–30 (1988)) to promote a more rapid healing of damaged tissue.

It is also useful to coadminister the 2'-deoxyribonucleosides of the invention with topical corticosteroid and antiinflammatory agents to accelerate the healing of lesions in patients suffering from allergic or inflammatory processes, since steroids are known to slow the healing of wounds.

The compositions of the invention are particularly useful in conditions in which normal wound healing is impaired. Examples of types of wounds that heal poorly or slowly include venous stasis ulcers, decubitus ulcers, and cutaneous and alimentary tract wounds or ulcers in patients with diabetes, and in patients subjected to irradiation, cancer chemotherapy (e.g. with adriamycin or cyclophosphamide), and topical or systemic anti-inflammatory glucocorticosteriods.

The following compounds may also be useful to combine or coordinate with the 2'-deoxyribonucleosides in the treatment of wounds. These compounds may be used in parallel or in series with the 2'-deoxyribonucleosides. They include, but are not limited to: allantoin, retinoic acid, aloe vera, glycine, vitamin A, the B vitamins, especially nicotinamide, vitamins C and E, antibacterial agents (e.g., quaternary ammonium compounds, bacitracin, neomycin and polymyxin), comfrey root preparations, platelets and/or platelet extracts, ribonucleosides, collagen, proline, lysine, elastin, fibronectin, glycosaminoglycans, spermidine (and other polyamines), angiogenic factors, zinc, sucrose, and various peptide growth factors such as the somatomedins, Iamin, EGF, the IGF's, PDGF, FGF, EDGF, TGF, CDGF, MDGF, and NGF. The compositions of the invention may also be used in conjunction with synthetic skin in treating burns and other wounds, and in supporting the healing of skin or corneal transplants.

For treatment of gastric or duodenal ulcers, the 2'-deoxyribonucleosides of the invention can be coadministered with other anti-ulcer agents. Such agents include, but are not limited to, cimetidine, ranitidine, omeprazole, sucralfate (an ulcer adherent complex), misoprostil (a cytoprotective prostaglandin), or antacids.

The 2'-deoxyribonucleoside-carrier composition may be formulated as part of a suntan lotion that may be applied before or after exposure to sunlight. The suntan lotion may also comprise one or more sun blockers such as PABA, esters of PABA, and other non-PABA chemical sunscreens. Compositions for treatment or amelioration of the effects of aging may be applied locally, in the form of a skin lotion.

The deoxyribonucleosides, incorporated into a suitable ophthalmic ointment, solution, or insert, may also be used to treat corneal lesions or ulcers such as may result from chemical damage, surgery, injury, burns, or infection. Such compositions may also be used to improve the healing between transplanted corneas and recipient sites.

The deoxyribonucleoside compositions may be incorporated into space-filling surgical implants or bone matrix implants in order to accelerate or improve the ingrowth of granulation or connective tissue.

Medical or veterinary indications for the use of the invention include but are not limited to the following situations. The compositions may be used to accelerate the healing of mechanical wounds or abrasions of the skin or other tissues which are exposed by mechanical injury to the skin or gastrointestinal mucosa of the body. The invention may be used to accelerate the healing of burns inflicted upon the skin, and any underlying tissues which may be exposed by such injury. The burns may be those caused by heat, ionizing radiation, ultraviolet radiation including sunlight, electricity, or chemical substances.

Further, the compositions may be used to accelerate the healing of surgical incisions in any part of the body, external or internal, into which a solution or other carrier composition containing the deoxyribonucleosides of the invention may be introduced. The compositions may be used to accelerate the healing of ischemic ulcers, pressure sores, bed sores, or ulcers caused by diabetes or other disease processes. They may also be used to treat mucosal lesions or ulcers (e.g., in mouth, stomach, or intestines). This may involve incorporation of the deoxyribonucleosides in a suitable mucilaginous or colloidal dispersion, or demulcent base, that may be administered orally, resulting in local delivery of the nucleosides to the desired sites in the alimentary tract.

In promoting the healing of skin wounds, including surgical incisions, it is best to apply the compounds of the invention locally, either in an ointment or in a wound dressing. A topical antibiotic or antiviral agent might be coadministered. The molar equivalent of 0.1 to 20 mg of a mixture of deoxyribonucleosides according to the compositions of the invention should be applied per square cm of wound area, or 0.1 to 10 mg per cm of linear incision.

The following examples are illustrative, but not limiting of the methods and compositions of the present invention. Other suitable modifications and adaptations of a variety of conditions and parameters normally encountered in clinical therapy which are obvious to the those skilled in the art are within the spirit and scope of this invention.

EXAMPLE 1

Forty-eight male F344 rats weighing approximately 150 grams were anesthetized with a combination of ketamine (100 mg/kg) and xylazine (13 mg/kg) administered by i.p. injection. The back of each rat was shaved, and an 8 mm diameter dorsal lumbar circular excision (full thickness) wound made, exposing the underlying superficial skeletal muscle. An 8 mm agarose (1%) disc containing one or some combination of the four principal 2'-deoxyribonucleosides or left blank (control) was placed in each wound. The concentration of each nucleoside was 30 mg/ml of physiological saline. The wounds were then covered with a liquid plastic dressing.

After two days, the wound were uncovered, the agarose disc removed, the wound photographed and scored for extent of healing. An alginate gel (2%) containing the same nucleoside or combination of nucleosides was then applied to each wound and the wounds again covered with a liquid plastic. On the fourth day following wounding, the wounds were again uncovered, the alginate gel removed and the wounds scored for extent of healing. Three animals were used in each of 16 groups. Each group received either one, two, three, or all four of the 2'-deoxyribonucleosides deoxythymidine, deoxycytidine, deoxyguanosine, and deoxyadenosine in all of the possible combinations.

TABLE 1

| | | Score | |
|---|---|---|---|
| | Treatment | Day 2 | Day 4 |
| 1 | Control | 0 | 2.33 |
| 2 | dA | 0 | 3.00 |
| 3 | dC | 0 | 0 |
| 4 | dG | 0 | 2.00 |
| 5 | dT | 0 | 0 |
| 6 | dT, dC | 0 | 2.00 |
| 7 | dG, dA | 1.50 | 2.50 |
| 8 | dT, dA | 0.33 | 1.66 |
| 9 | dT, dG | 0.66 | 1.80 |
| 10 | dC, dG | 3.33 | 3.33 |
| 11 | dC, dA | 0.66 | 2.50 |
| 12 | dC, dG, dA | 2.00 | 3.66 |
| 13 | dT, dG, dA | 0.33 | 2.66 |
| 14 | dT, dC, dG | 3.00 | 3.00 |
| 15 | dT, dC, dA | 0.66 | 2.50 |
| 16 | dA, dC, dG, dT | 4.00 | 4.00 |

Wound Healing Scale:
0 = no connective tissue in wound area.
1 = connective tissue covering less than 50% of wound.
2 = connective tissue covering 50–100% of wound.
3 = connective tissue covering wound area completely.
4 = connective tissue filling the entire wound, completely opaque.

Of the six different combinations of two 2'-deoxyribonucleosides, only the combination of dC and dG is more effective in promoting the development of connective tissue after 48 and 96 hours compared to the controls. Of the four different combinations of three 2'-deoxyribonucleosides, only the combinations that included dC and dG (dC, dG, dA and dC, dG, dT) were more effective in promoting wound healing than control after 48 and 96 hours. None of the individual 2'-deoxyribonucleosides or combinations of two or three 2'-deoxyribonucleosides were as effective in promoting the development of connective or granulation tissue as was the combination of all four of the principal 2'-deoxyribonucleosides at 48 or 96 hours.

EXAMPLE 2

A study was conducted to compare the healing effects of the four principal deoxyribonucleosides (dA, dC, dG, and dT) with the corresponding monophosphate deoxyribonucleotides.

Eight male F344 rats weighing approximately 200 grams each were anesthetized with a combination of ketamine (100 mg/kg) and xylazine (13 mg/kg) and their backs shaved. Standard 8 mm diameter full-thickness wounds were made on the back of each rat. An agarose disc containing either all four deoxyribonucleosides (dA, dC, dG, and dT) (n=3) or all four corresponding deoxyribonucleotides (dAMP, dCMP, dGMP, and dTMP) in a concentration of 30 mg/ml of physiological saline (n=4), or a blank agarose disc (n=2) was placed in each wound. All wounds were then covered with methacrylate. On post-wounding day 2, each wound was treated with an alginate gel containing either nucleosides, nucleotides, or nothing at all. Wounds were uncovered, examined, and scored for extent of healing on days 2 and 4. In addition, on day 4 the skin surrounding the wound and the wound area itself were removed and placed in 10% formalin for histological examination. Results after 2 days Both controls were scored 0. Both of the nucleoside-treated wounds were scored 3+ (completely covered and opaque in some areas). All four of the wounds treated with the nucleotides were also scored 3+. All of the treated wounds were quite indistinguishable after 48 hours. Results after 4 days Both of the controls were scored 2–3 (completely covered, but the tissue was very thin and fragile). The nucleoside-treated wounds were rated 3+ and 4. All four of the nucleotide-treated wounds were scored 2–3. They were indistinguishable from controls. They did not appear to be as well developed as they were on day 2. The connective tissue covering these wounds was noticeably thinner and less durable than that covering the nucleoside-treated wounds.

EXAMPLE 3

Acute toxicity test of deoxyribonucleoside mixture

A mixture of equimolar amounts of deoxyadenosine, deoxyguanosine, deoxycytidine, and thymidine was suspended in water and administered to groups of 200 gram male F344 rats by oral intubation. During the observation period of one week following administration, no signs of toxicity or death were observed at any dose, including 10 g/kg, the highest dose tested. Accordingly, the 50% lethal dose (LD50) is demonstrated to be greater than 10 g/kg.

EXAMPLE 4

Glucocorticosteroids, which are widely used in clinical therapy, are known to retard the wound-healing process in humans and animals. Corticosteroid treatment is also a standard model for impaired wound healing. The purpose of this experiment was to test the efficacy and safety of the combination of the four principal deoxyribonucleosides in overcoming steroid-induced impairment of the healing of dermal ulcers.

Fourteen male F344 rats weighing approximately 200 grams each (8 weeks of age) were treated with dexamethasone (5 mg/kg i.p.). Twenty-four hours later, a standard, full-thickness 8 mm circular midline excision wound was made in the dorsal cervical region. Fifty microliters of a combination of deoxyadenosine, deoxycytidine, deoxyguanosine, and deoxythymidine (0.025/ml each) in a hydrogel vehicle or the vehicle alone were applied to wounds on the day of surgery and once every 48 hours thereafter. Wounds were covered with a liquid plastic dressing as described by Marshak [Proc. Soc. Exp. Biol. Med. 58: 63–65 (1945)]. Following macroscopic examination and photographing, the wounds and surrounding tissues were collected 7 days after wounding for microscopic and histopathological evaluation. Tissue sectioning and evaluation were performed by Pathology Associates Inc., Frederick Md.

Figure 2:
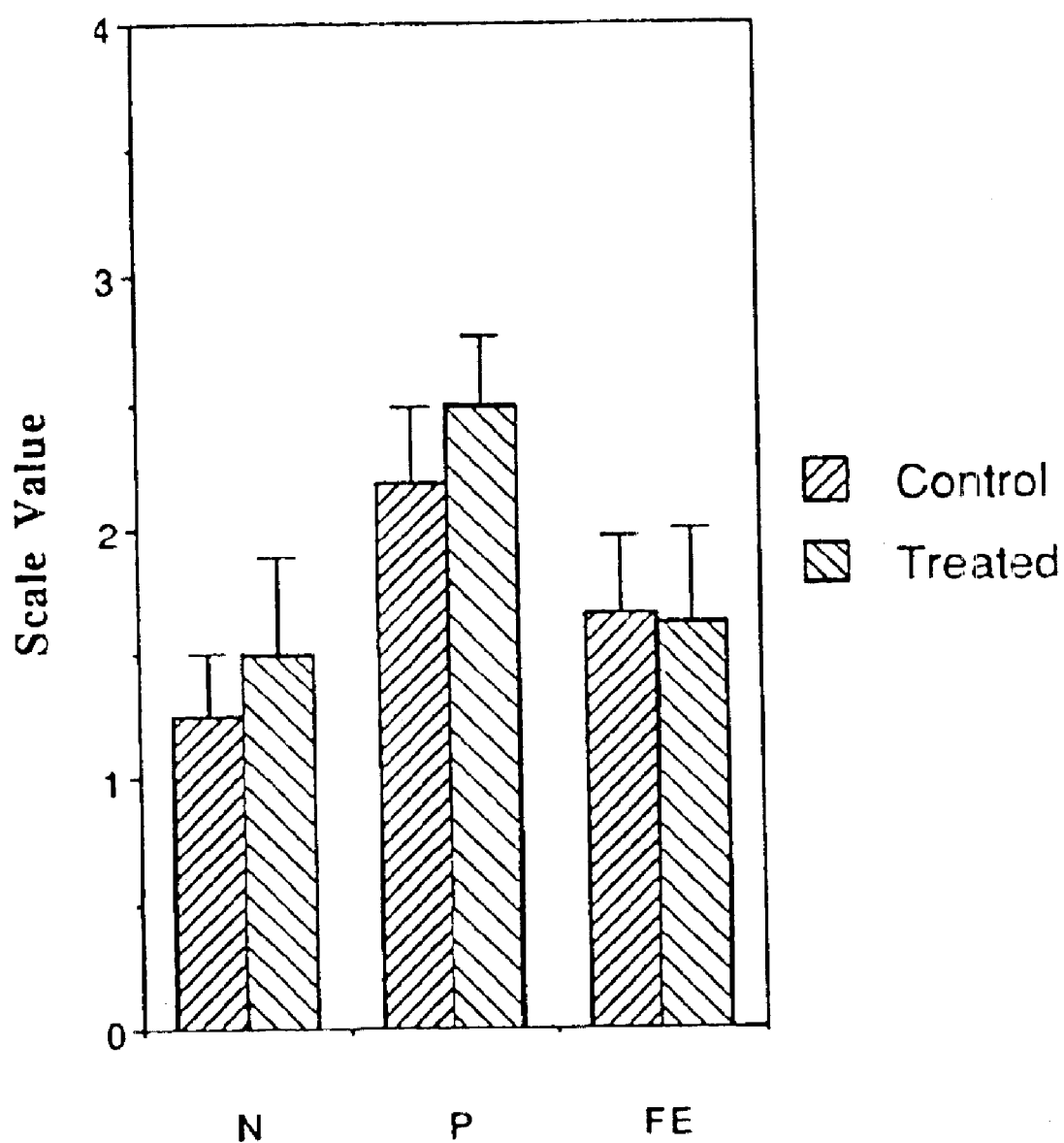
FIG. 2 shows the scale values for three indices of inflammation, necrosis (N), polymorphonuclearluekocyte density (P), and fibrinous exudate (FE), in control rats and rats treated with the combination of 2'-deoxyadenosine, 2'-deoxycytidine, 2'-deoxyguanosine, and 2'-deoxythymidine for one week. All rats were pre-treated with dexamethasone in order to retard wound healing. Scale values are: 0=absent, 1=minimal, 2=mild, 3=moderate, and 4=marked.

The results are presented in FIGS. 1 and 2. A semiquantitative method was used to evaluate: the extent of angiogenesis and re-epithelialization; the number of macrophages and fibroblasts in each wound; the degree of tissue and cellular necrosis; infiltration by polymorphonuclear leukocytes (PMN's); and the amount of fibrinous exudate. The indices of wound healing in those wounds treated with the deoxyribonucleosides were all significantly greater ($P<0.001$) than in wounds treated with the vehicle alone (FIG. 1). The extent of tissue necrosis, accumulation of fibrinous exudate, and infiltration of the wound by PMN's were not different between control and treated groups (FIG. 2), indicating that the deoxyribonucleosides do not elicit excess inflammation in these wounds. Histopathological analysis revealed normal cell and tissue morphology in all wound samples.

The differences in the extent of healing of the deoxyribonucleoside-treated wounds compared to the wounds treated with vehicle alone were striking at the gross macroscopic level. The day-seven appearance of the control wounds was very similar to that at the time of wounding, having, at best, very small areas of granulation tissue and minimal development of new epithelium. The nucleoside-treated wounds, in contrast, were all completely covered with a thick bed of granulation tissue. New epithelium covered more than 50% of the initial area of these wounds.

Therefore, application of the combination of the four principal deoxyribonucleosides to full thickness wounds overcomes the wound-healing impairment induced by dexamethasone, with no apparent deleterious effects, greatly accelerating the rate of wound healing.

EXAMPLE 5

The purpose of this experiment was to evaluate the efficacy and safety of the combination of the four principal deoxyribonucleosides in accelerating the wound healing process in young, normal rats, which are known to heal rapidly without intervention.

Thirty-six male F344 rats weighing approximately 200 grams each (8 weeks of age) were each given a standard, full-thickness 8 mm circular midline excision wound in the dorsal cervical region. Fifty microliters of a combination of deoxyadenosine, deoxycytidine, deoxyguanosine, and deoxythymidine (0.025/ml each) in a hydrogel vehicle or the vehicle alone were applied to wounds on the day of surgery and once every 48 hours thereafter. Wounds were covered with a liquid plastic dressing as described by Marshak [Proc. Soc. Exp. Biol. Med. 58: 63–65 (1945)]. Following macroscopic examination and photographing, the wounds and surrounding tissues were collected five (n=8 per group) and seven (n=10 per group) days after wounding for microscopic and histopathological evaluation. Tissue sectioning and evaluation was performed by Pathology Associates Inc., Frederick Md.

Figure 3:
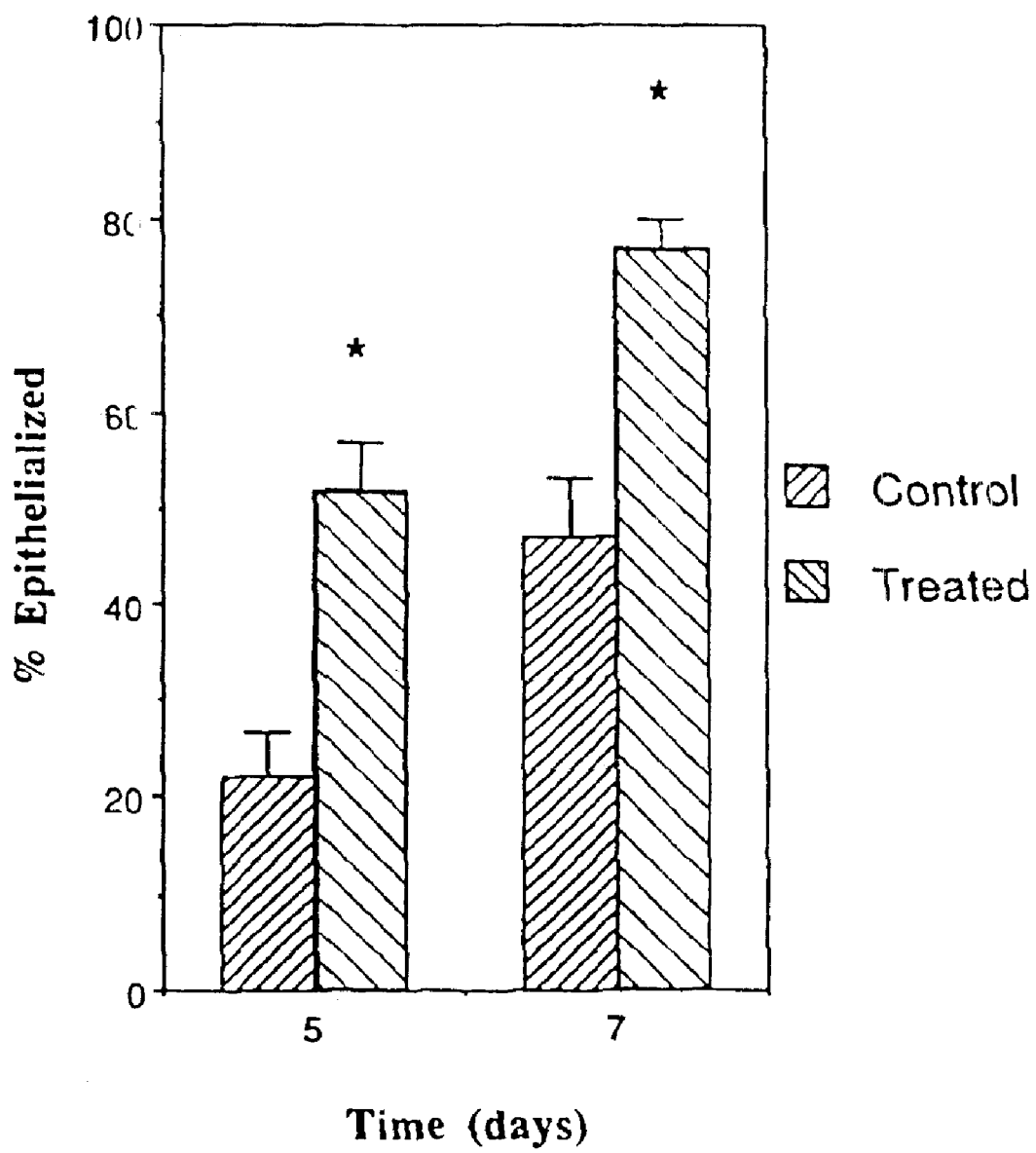
FIG. 3 shows the percentage of the original wound area covered by new epithelium in rats 5 and 7 days after initiating treatment with vehicle alone (control) and with the combination of 2'-deoxyadenosine, 2'-deoxycytidine, 2'-deoxyguanosine, and 2'-deoxythymidine.
Figure 4:
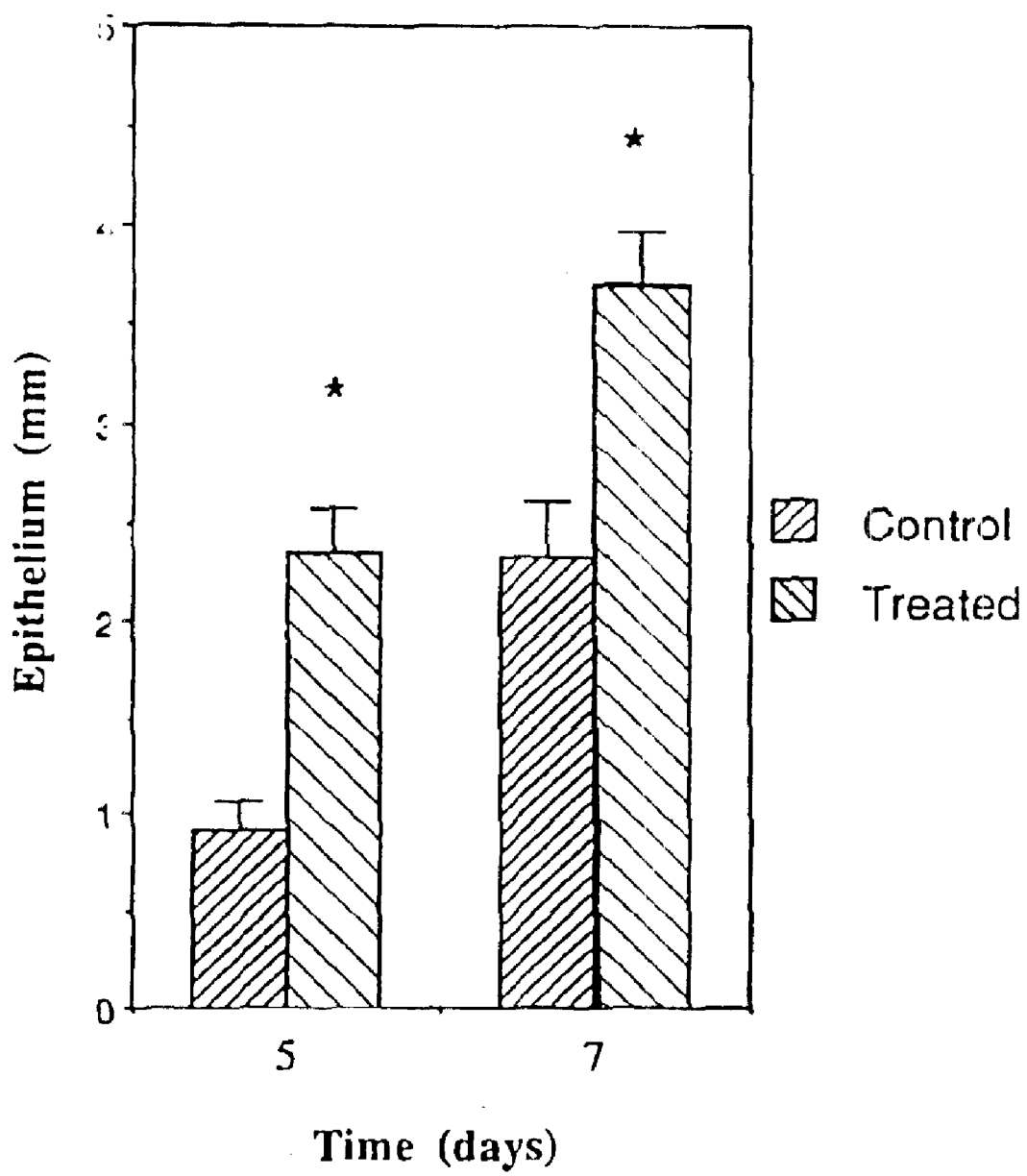
FIG. 4 shows the length of the new epithelium growing in from the wound margins (in histological cross-section) in rats 5 and 7 days after initiating treatment with vehicle alone (control) and with the combination of 2'-deoxyadenosine, 2'-deoxycytidine, 2'-deoxyguanosine, and 2'-deoxythymidine.
Figure 5:
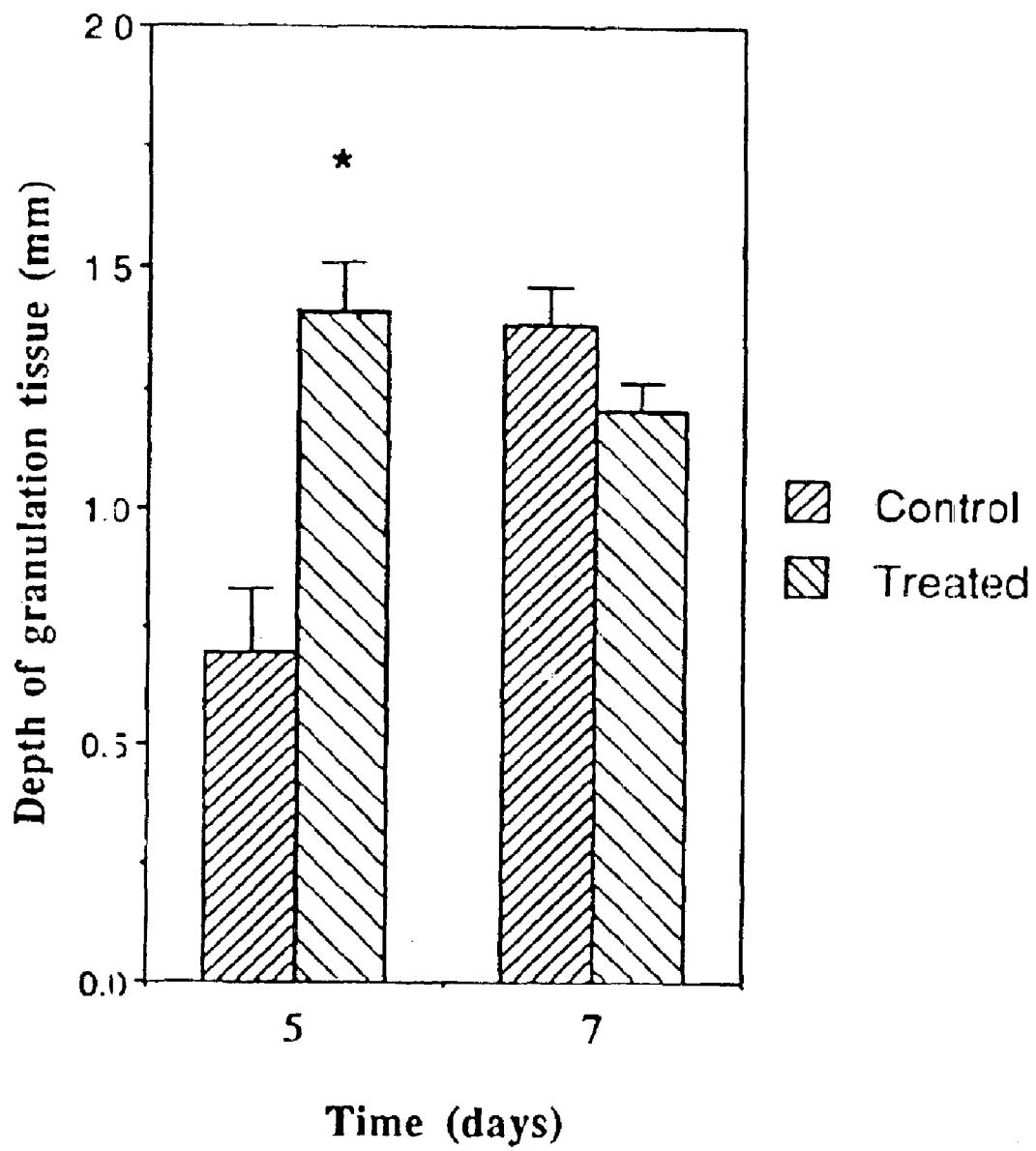
FIG. 5 shows the depth of the granulation tissue (in histological cross-section) in the wounds of rats 5 and 7 days after initiating treatment with vehicle alone (control) and with the combination of 2'-deoxyadenosine, 2'-deoxycytidine, 2'-deoxyguanosine, and 2'-deoxythymidine.

On both days 5 and 7 the macroscopic appearance of the nucleoside-treated wounds showed a markedly greater degree of granulation tissue formation and re-epithelialization than the vehicle-treated control wounds. The results of the microscopic and histopathological evaluation are presented in FIGS. 3, 4 and 5 and corroborate the macroscopic observations. On day 5 and on day 7 the percentage of the wound with new epithelium was significantly greater ($P<0.001$ and $P<0.01$, respectively) in the nucleoside treated group than in the vehicle-treated controls. Likewise, the absolute length of the new epithelium from the wound margins was significantly greater in the nucleoside-treated group on both day 5 ($P<0.001$) and day 7 ($P<0.005$) than in the control group. The depth of the granulation tissue (FIG. 5) was also significantly greater ($P<0.001$) in the nucleoside-treated group than in the control group on day 5. By day 7 the granulation tissue in the control wounds had reached a depth equivalent to that of the experimental group on day 5. The depth of granulation tissue in the nucleoside-treated group was not different than that seen at day 5 in this group. Histopathological evaluation revealed normal cell and tissue morphology and normal levels of inflammation in both the control and nucleoside-treated wounds and surrounding tissue.

These data indicate that treatment of full-thickness dermal ulcers in young, normal rats with a combination of deoxyadenosine, deoxycytidine, deoxyguanosine, and deoxythymidine significantly accelerates the rate of normal healing. Treated wounds were as well healed by day 5 as controls were on day 7. This represents a 28.6% increase in the rate of healing over the course of one week in young, normal animals.

EXAMPLE 6

1. Preparation of Liposomes Containing Deoxyribonucleosides

Liposomes or other biodegradable vesicles containing deoxyribonucleosides may be utilized with advantage, in order to provide prolonged delivery of deoxyribonucleosides to wound tissues.

The following protocol for liposome preparation was adapted from Szeka and Papahadjopoulos (PNAS 75:4194–4198 (1978)). Other methods for preparation of liposomes (and various other lipid components) may also be used to prepare vesicles containing deoxyribonucleosides.

Cholesterol (50 micromoles), phosphatidylcholine (40 micromoles), and phosphatidylglycerol (10 micromoles) were dissolved in chloroform (5 ml) and diethyl ether (5 ml) in a 50 ml round-bottom flask. The flask was capped and purged with nitrogen. 1.5 ml of an aqueous solution containing deoxyribonucleosides, (e.g. 10 mg/ml of deoxyadenosine, deoxycytidine, deoxyguanosine, and thymidine in 15 mM NaCl) was added to the organic phase. The mixture was sonicated for 5 minutes at 0–5 degrees C. in a bath sonicator until the 2-phase system becomes a homogenous dispersion. A probe sonicator may also be used. The organic solvents were removed with rotary evaporator under reduced pressure (e.g. a water aspirator) at 35–40 degrees C., rotating at about 200 rpm. The mixture initially frothed, then became a viscous gel, and finally, it became an aqueous suspension. At this point, 2 ml of saline solution were added, and the suspension was evaporated for an additional 15 minutes to remove remaining traces of ether or chloroform. The preparation was then centrifuged, to separate the liposomes from non-encapsulated material. 35 to 40% of the original deoxyribonucleoside solution was encapsulated within the liposomes. Following purification, the liposomes were concentrated by centrifugation, and suspended in 3 ml physiological saline for topical application to wounds.

The deoxyribonucleoside-containing liposomes can also be suspended in ointments, creams, or other delivery vehicles for topical application to wounds, damaged skin, or ulcers.

2. Effect of Liposomes Containing Deoxyribonucleosides on Wound Healing

Liposomes can be effective vehicles for the delivery of a variety of pharmaceutical compounds. The purpose of this experiment was to evaluate liposomes as potential delivery vehicles for the topical application of the deoxyribonucleosides to dermal wounds.

Fourteen male F344 rats weighing approximately 200 grams each (8 weeks of age) were each given a standard, full-thickness 8 mm circular midline excision wound in the dorsal cervical region. A combination of deoxyadenosine, deoxycytidine, deoxyguanosine, and deoxythymidine (0.010/ml each) were incorporated into liposomes as described. Blank liposomes (made with saline solution only) or liposomes containing the deoxyribonucleosides were applied to the wounds on the day of surgery and once every 48 hours thereafter. Wounds were covered with a liquid plastic dressing as described by Marshak [Proc. Soc. Exp. Biol. Med. 58: 63–65 (1945)]. Seven days after wounding, the wounds were examined macroscopically for the degree of granulation tissue formation and extent of re-epithelialization.

The amount of granulation tissue present and the extent of new epithelium that had begun to cover the wounds treated with the nucleoside-containing liposomes was significantly greater than in the wounds treated with the blank liposomes only. These results show that liposomes containing deoxyribonucleosides are useful embodiments of the Invention.

EXAMPLE 7

In order to test the efficacy of the combination of the four principal deoxyribonucleosides in the healing of mucosal wounds, the rat chronic gastric ulcer model of Okabe et al. [Digestive Diseases 16:227–284 (1971)] was utilized.

Forth-eight male F344 rats weighing approximately 190 grams were anesthetized with a combination of ketamine (100 mg/kg) and xylazine (13 mg/kg) administered by i.p. injection. The ventral surface of each rat was shaved and treated with an antibacterial solution. The stomach was then exposed through a ventral incision, a 7 mm (internal diameter) plastic cylinder placed on the serosal surface at the border of the corpus and the antrum of the stomach, and 0.07 ml acetic acid applied for 1 minute. The acid-treated area was then thoroughly rinsed with sterile saline, and the ventral incision closed. Treatment began 5 days later.

The treatment agent was prepared by mixing 1.25 grams (each) of deoxyadenosine, deoxycytidine, deoxyguanosine, and deoxythymidine in a demulcent base consisting of 0.27 grams (each) of carboxymethylcellulose and gum xanthan in 50 ml of sterile water. The control preparation consisted of the carboxymethylcellulose and gum xanthan vehicle. Rats received 1 ml of either the treatment or control agent twice daily (morning and late afternoon) by oral intubation. Animals were fed standard laboratory rat chow. Food and water were available ad libitum. On days 10, 20, and 30, eight animals from each group were sacrificed, and their stomachs removed. Following light fixing in 1% formalin, the ulcer area (the area of the ulcer base remaining without new epithelial coverage) was measured and recorded for each ulcer.

Figure 6:
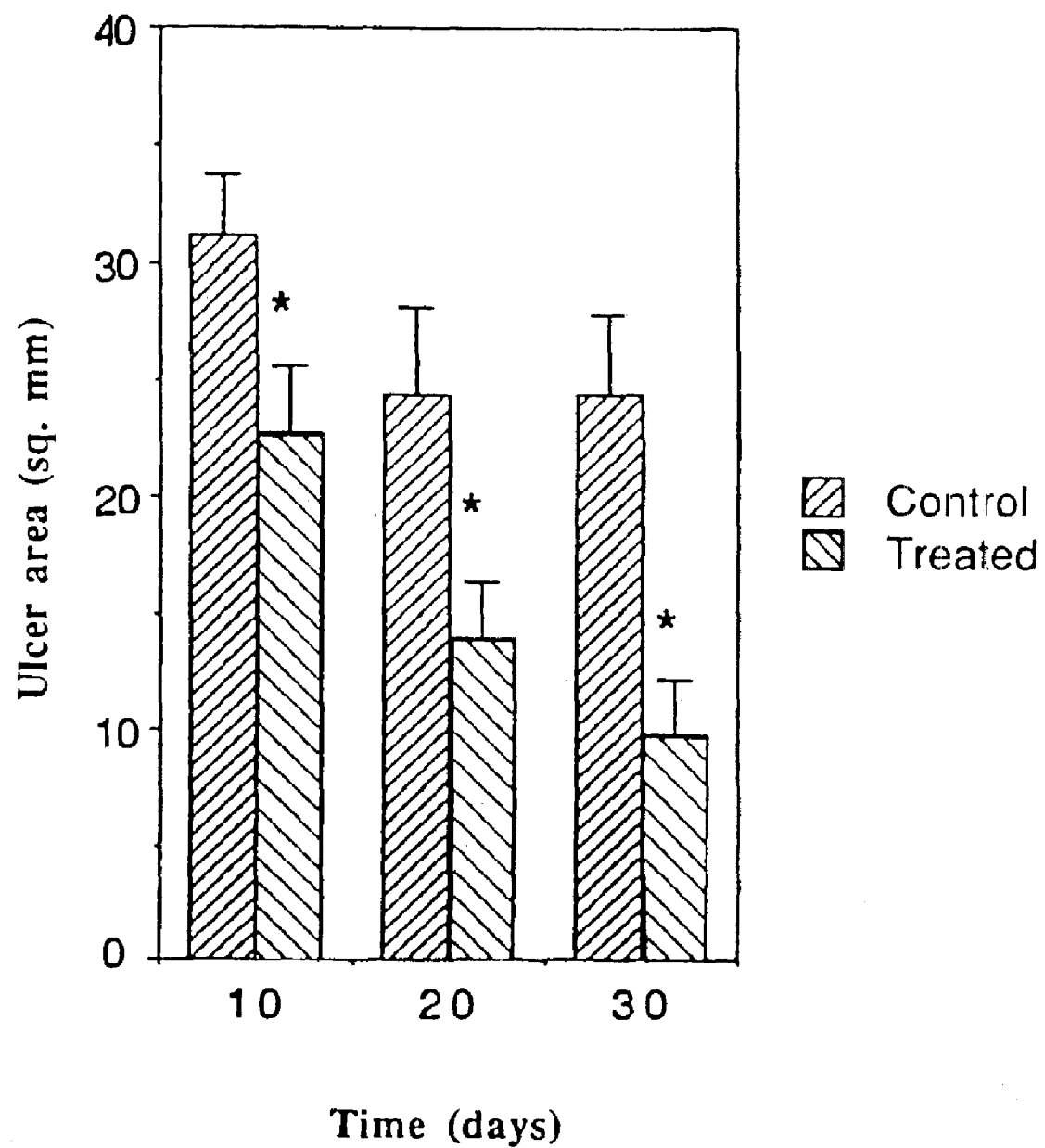
FIG. 6 shows the gastric ulcer area (the area of the ulcer remaining unepithelialized) of control rats and rats treated with the combination of 2'-deoxyadenosine, 2'-deoxycytidine, 2'-deoxyguanosine, and 2'-deoxythymidine 10, 20, and 30 days after initiating treatment.

The results of this experiment are displayed in FIG. 6. At each point the ulcer area was significantly smaller in the treated group compared to the control group. These data demonstrate the efficacy of the deoxyribonucleoside preparation in accelerating the healing of gastric mucosal ulcers.

EXAMPLE 8

Standard laboratory rat chow used in the initial gastric ulcer experiments (see Example 7 above) contains a great deal of fiber and roughage that is known to irritate healing gastric ulcers in rats, thereby complicating the healing process. Therefore, the effect of deoxyribonucleosides on the healing of gastric ulcers was examined in rats receiving a soft, agar-based rat food, which eliminated any potential complications created by the standard laboratory rat chow diet.

Sixty male F344 rats received gastric ulcers according to the protocol described in Example 7 above. The animals were fed a diet consisting Bioserv Basal Gel Diet (Bioserv, Inc., Frenchtown, N.J.). Food and water were available ad libitum. The animals were treated with vehicle alone (carboxymethylcellulose and gum xanthan) or a combination of deoxyadenosine, deoxycytidine, deoxyguanosine and deoxythymidine in gum xanthan and carboxymethylcellulose, as described in Example 7. Fifteen animals in each group were sacrificed on days 10 and 16 of treatment. The ulcer area remaining non-epithelialized in each stomach was measured and recorded.

Figure 7:
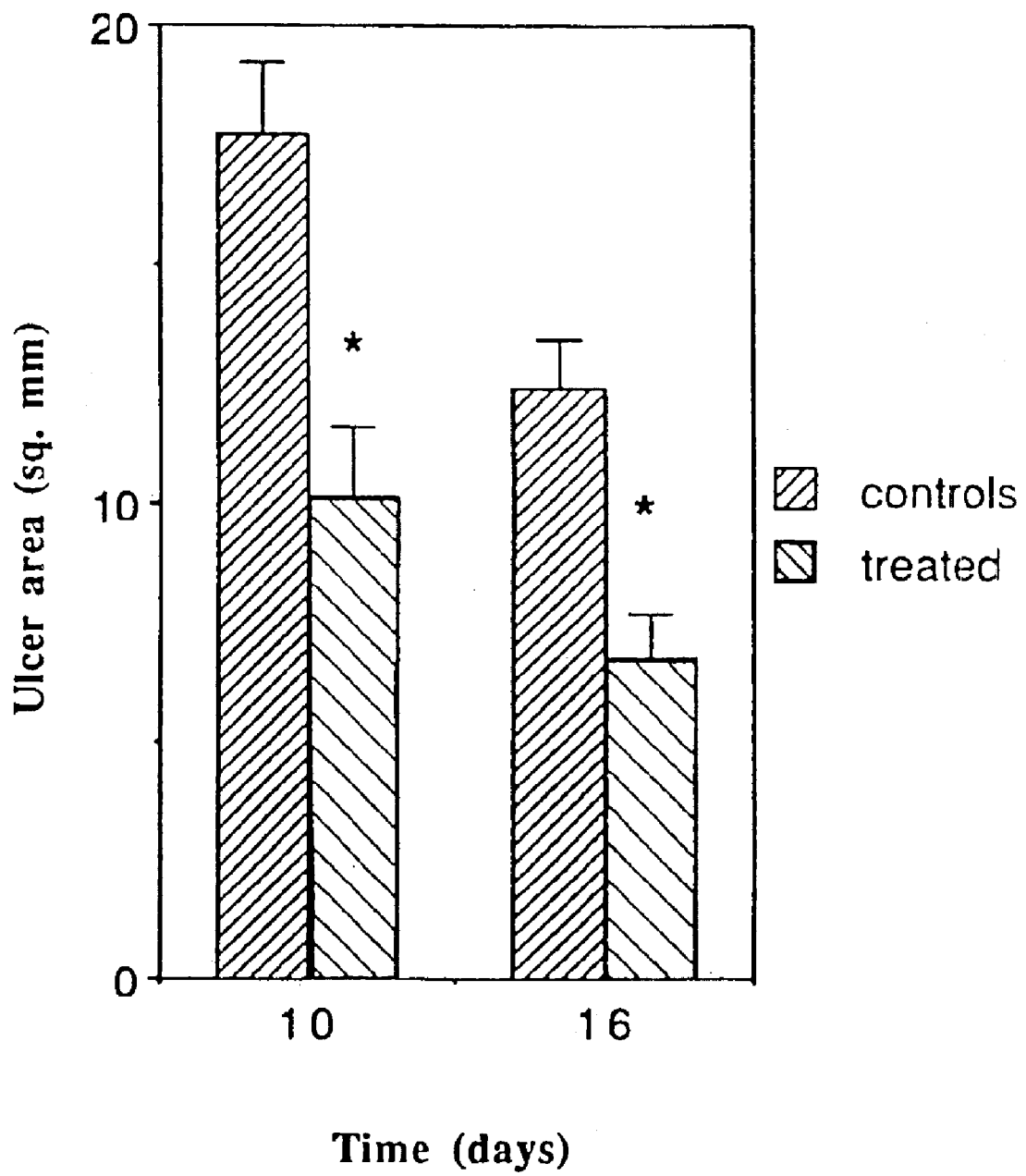
FIG. 7 shows the gastric ulcer area of control rats and rats treated with the combination of 2'-deoxyadenosine, 2'-deoxycytidine, 2'-deoxyguanosine, and 2'-deoxythymidine after 10 and 16 days of treatment.

The results, as illustrated in FIG. 7, show that, while the rate of healing of both control and treated ulcers was greater than that seen when using standard laboratory rat chow (FIG. 6), treatment of these mucosal wounds with the deoxyribonucleoside preparation accelerated the healing process significantly compared to vehicle-treated control ulcers at both 10 and 16 days. ($P<0.002$ and $P<0.001$, respectively). Microscopic examination and histopathology confirmed our macroscopic findings of significantly greater epithelialization of the treated ulcers, and revealed that cell and tissue morphology were normal in both control and treated ulcers.

EXAMPLE 9

Cimetidine is known as an effective anti-ulcer agent. The mechanism of action of cimetidine is primarily inhibition of gastric acid secretion via its action at gastric histamine ($H_2$) receptors. This provides a less hostile gastric milieu for the ulcer to heal, but does not necessarily directly stimulate the healing process itself. Agents which directly accelerate the healing processes should produce effects on gastric ulcer healing greater than those obtained by cimetidine treatment alone. Therefore, the effects of cimetidine and a deoxyribonucleoside preparation, alone and in combination, on gastric ulcer healing were investigated.

Fifty-one male F344 rats were given gastric ulcers according to the method described in Example 7. Five days later treatment began. Animals received in 1 ml of either vehicle alone (carboxymethylcellulose and gum xanthan; see Example 7 above), a combination of deoxyadenosine, deoxycytidine, deoxyguanosine, and deoxythymidine (0.025 grams/ml of each) in the vehicle, cimetidine (15 mg/ml) in the vehicle, or cimetidine plus the deoxyribonucleosides in the vehicle. Treatments were administered twice daily, in the morning and late afternoon, by oral intubation. Rats were treated for 14 days and then sacrificed. Stomachs were removed and lightly fixed with 1% formalin. The remaining ulcer and surrounding tissues were then excised and the areas of the ulcers remaining non-epithelialized were determined. Samples were stored in 10% formalin.

Figure 8:
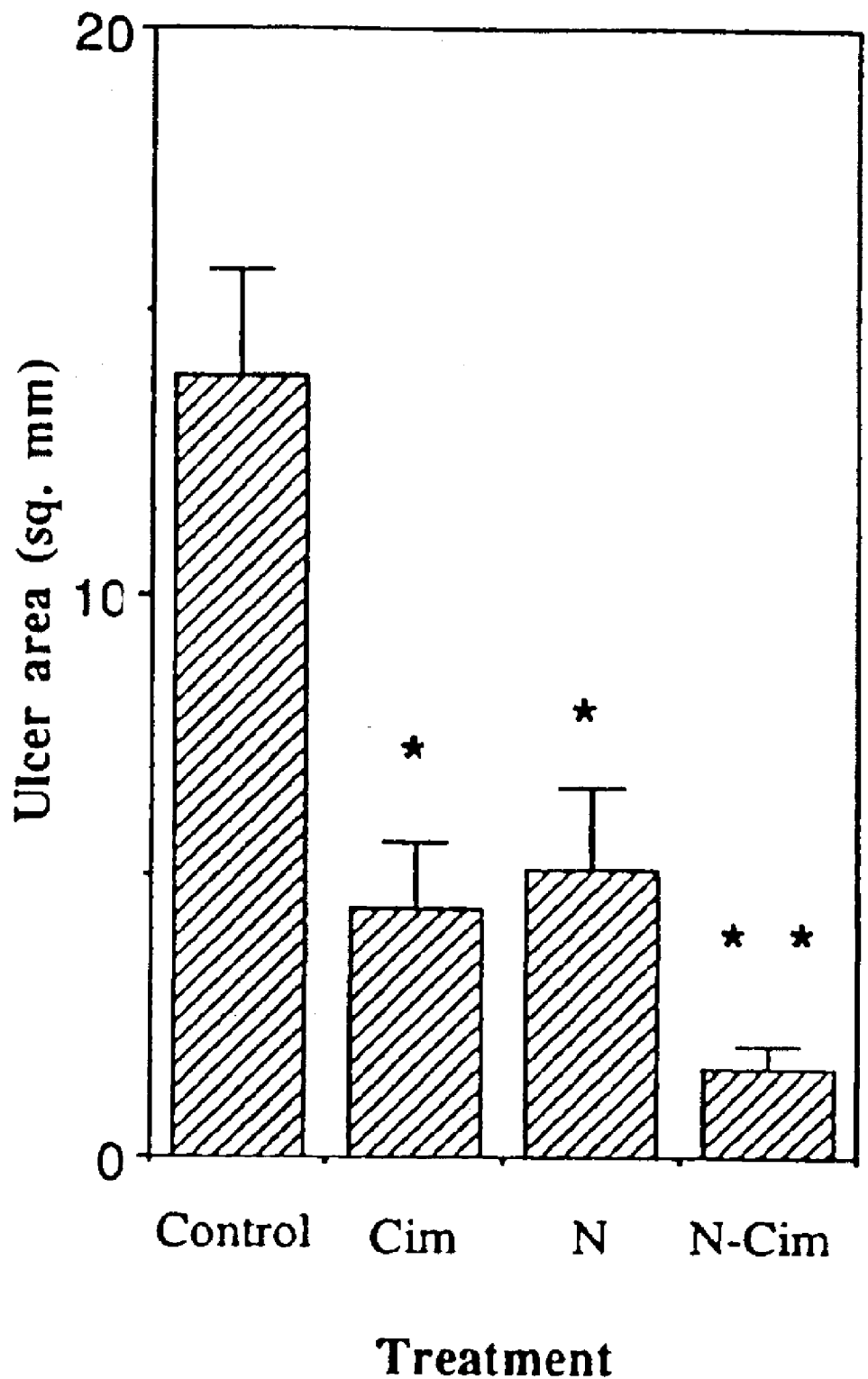
FIG. 8 shows the gastric ulcer area of control rats, rats treated with cimetidine (Cim), rats treated with the combination of 2'-deoxyadenosine, 2'-deoxycytidine, 2'-deoxyguanosine, and 2'-deoxythymidine (N), and rats treated with both cimetidine and the 2'-deoxyribonucleosides (N-Cim) 14 days after treatment began. The * indicates statistically significant differences compared to control values, while ** indicates statistically significant differences compared to Cim-and N-treated values.

The results of this experiment are shown in FIG. 8. The area of both the cimetidine-treated and deoxyribonucleoside-treated ulcers was significantly reduced compared to the vehicle-treated (control) ulcers ($P<0.001$ and $P<0.002$, respectively). The ulcers treated with cimetidine plus the deoxyribonucleosides were not only significantly smaller than controls ($P<0.001$), but were also significantly smaller than the ulcers treated with cimetidine ($P<0.05$) or with the deoxyribonucleoside preparation ($P<0.05$). Thus, it appears that the deoxyribonucleosides act by a different mechanism than that of cimetidine, and that the combined treatments have additive effects in promoting the healing of chronic gastric ulcers.

EXAMPLE 10

Japanese patent J 60028929-A, assigned to Hokuriku Pharm. KK claims to be a remedy for peptic ulcers, although only data on the partial prevention of acute stress-induced ulcers were disclosed. This remedy contains 2'-deoxyguanosine. The purpose of this experiment was to compare the efficacy of deoxyguanosine alone with the efficacy of the combination of the 2'-deoxyribonucleosides of adenine, cytidine, guanine, and thymine in treating chronic gastric ulcers.

Forty-eight F344 male rats weighing approximately 210 grams each were given gastric ulcers by the acetic acid method described in Example 7 above. Treatment was begun 5 days after initiating the ulcers and was done according to the method and schedule described previously. Animals received 1 ml of either the vehicle alone (control), the four deoxyribonucleosides in the vehicle (0.025 grams/ml of each), or deoxyguanosine (0.025 grams/ml) in the morning and in the late afternoon daily for 14 days. On the final day of treatment all 16 animals in each group were sacrificed, their stomachs removed and light fixed in formalin, and the ulcer areas remaining non-epithelialized were measured and recorded.

Figure 9:
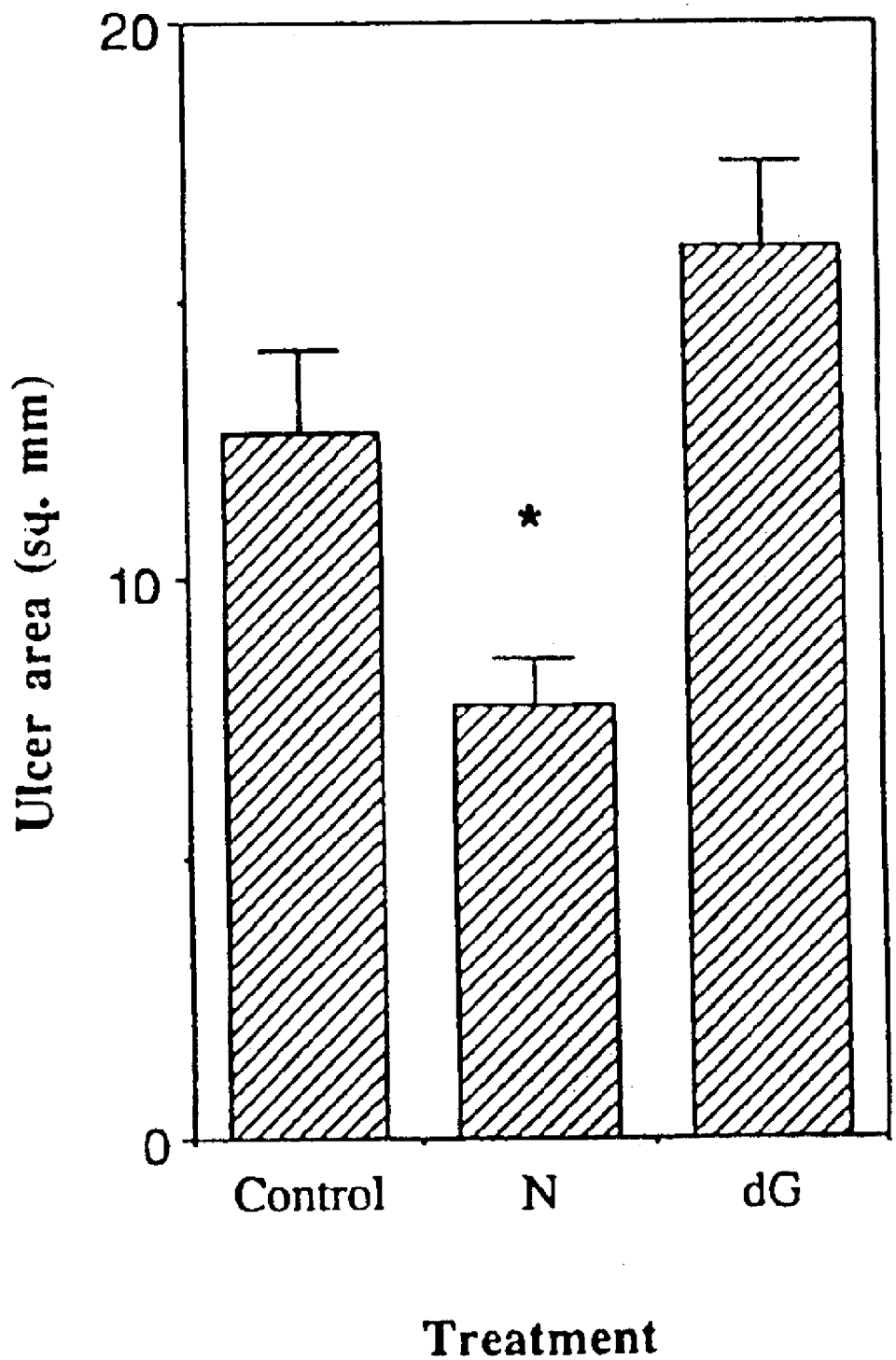
FIG. 9 shows the gastric ulcer ar a of control rats, rats treated with the combination of 2'-deoxyadenosine, 2'-deoxycytidine, 2'-deoxyguanosine, and 2'-deoxythymidine (N), and rats treated with 2'-deoxyguanosine alone (dG).

The results of this experiment are presented in FIG. 9. The ulcer area of the vehicle-treated controls was 12.6±1.5, while the area of those ulcers treated with all four deoxyribonucleosides was 7.7±0.87 ($P<0.01$) and of those treated with deoxyguanosine alone 16.3±1.5 ($P>0.05$). Thus, deoxyguanosine alone appears to be ineffective in treating chronic gastric ulcers, while the combination of deoxyadenosine, deoxycytidine, deoxythymidine, and deoxyguanosine is effective in accelerating the healing of these mucosal wounds.

What is claimed is:

1. A composition of matter in the form of a lotion, ointment, cream or gel, comprising,
    an active agent comprising
        (a) from 10 to 90 percent by mol 2'-deoxycytidine, and
        (b) from 90 to 10 percent by mol 2'-deoxyguanosine, or the pharmaceutically acceptable salts thereof, and
    a pharmaceutically acceptable carrier;
    wherein said active agent is present at a concentration such that said composition is capable of promoting wound healing in an animal, and wherein said carrier is adapted for local or topical administration.

2. A composition of matter as recited in claim 1 wherein each of said components is present in from 25 to 75 percent of said composition.

3. A composition of matter in the form of a lotion, ointment, cream or gel, consisting essentially of,
    an active agent comprising
        (a) from 10 to 90 percent by mol 2'-deoxycytidine, and
        (b) from 90 to 10 percent by mol 2'-deoxyguanosine, or the pharmaceutically acceptable salts thereof, and
    a pharmaceutically acceptable carrier;
    wherein said active agent is present at a concentration such that said composition is capable of promoting wound healing in an animal, and wherein said carrier is adapted for local or topical administration.

4. A composition of matter in the form of a lotion, ointment, cream or gel, comprising,
    an active agent comprising
        (a) from 10 to 90 percent by mol 2'-deoxycytidine, and
        (b) from 90 to 10 percent by mol 2'-deoxyguanosine, each of said 2'-deoxycytidine and 2'-deoxyguanosine being present as
            (i) the free from thereof, or
            (ii) a substituted derivative of (a) or (b),
    wherein one or both of said 2'-deoxycytidine and 2'-deoxyguanosine are substituted by one or more groups which may be the same or different, at one or both hydroxyl groups in the deoxyribose moiety and/or substituted in the exocyclic amine on the purine ring of 2'-deoxyguanosine or in the exocyclic amine on the pyrimidine ring of 2'-deoxycytidine by an acyl radicals containing 2 to 20 carbon atoms, or the pharmaceutically acceptable salts thereof, and
    a pharmaceutically acceptable carrier;
    wherein said active agent is present at a concentration such that said composition is capable of promoting wound healing in an animal, and wherein said carrier is adapted for local or topical administration.

5. A composition as in claim 1 further comprising 2'-deoxyadenosine.

6. A composition as in claim 1 further comprising 2'-deoxythymidine.

7. A composition as in claim 5 further comprising 2'-deoxythymidine.

* * * * *